US00PP08632P

United States Patent [19]

Steenks

[11] Patent Number: Plant 8,632

[45] Date of Patent: Mar. 8, 1994

[54] HYBRID TEA ROSE PLANT NAMED RUISTEENKA

[75] Inventor: J. E. Steenks, Baarlo, Netherlands

[73] Assignee: De Ruiter's Nieuwe Rozen B.V., Hazerswoude, Netherlands

[21] Appl. No.: 999,605

[22] Filed: Dec. 31, 1992

[51] Int. Cl.[5] ..... A01H 5/00

[52] U.S. Cl. ..... Plt./19

[58] Field of Search ..... Plt. 11, 19, 18, 20

*Primary Examiner*—Howard J. Locker

*Attorney, Agent, or Firm*—Christie, Parker & Hale

[57] ABSTRACT

A new variety of hybrid rose plant having dark pink flowers suitable for growing under glass.

2 Drawing Sheets

SUMMARY OF THE INVENTION

The present invention relates to a new and distinct variety of rose plant of the hybrid tea rose class, which was discovered by me as a natural whole plant mutation in a controlled planting of the variety known as 'Ruidriko' (U.S. Plant Pat. No. 7,362). The varietal denomination of the new variety is 'Ruisteenka'.

Among the novel characteristics possessed by this new variety which distinguish it from its parent and all other varieties of which I am aware are its attractive dark pink flowers borne on a plant having the same desirable qualities as its parent for production of cut flowers under glass. The new variety can be reproduced through propagation by cuttings, grafting, budding and micropropagation. Flowers of the new variety are produced on long strong stems. Asexual reproduction by budding, grafting, propagation of cuttings, and micropropagation of the new variety as performed in Hazerswoude, Holland shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions.

One illustration shows cut flower form of the new variety and the other illustration shows details of the new rose variety.

DETAILED DESCRIPTION OF THE NEW VARIETY

The following is a detailed description of my new variety, with color terminology in accordance with the Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart.

Parentage: Mutation of 'Ruidriko'.
Class: Hybrid tea.

As can be seen in the accompanying detail illustration there is shown the top of a young shoot, 1; compound three, five and seven leaflet leaves, 2, 3, and 4 respectively; a stem, 5; buds, 6 and 7; a flower, 8, about one-third open; and a flower 9, more fully open. Also shown are flower stems 10, 11 and 12, with reproductive organs displayed.

The following further horticultural observations were made of specimens grown under glass in Holland.

Flower

Blooming Habit: Nearly continuous.

A. Bud:

(1) *Size.*—Medium.

(2) *Form.*—Ovate (before separation of sepals); urn-shaped after sepals part.

(3) *Color.*—As sepals divide, bud color is near 37C to 37D with near 54A at edge and washing toward lower end of petal; deeper red coloration at bud tip of the petal margin.

(4) *Sepals.*—Shorter than bud, generally simple to slightly foliated.

(5) *Peduncle.*—Length — medium. Aspect — straight. Strength — erect, very strong. Color — medium green.

B. Bloom:

*Flower.*—Medium to large size; viewed from above — irregularly rounded; viewed from side — (a) upper part of fully opened flower, flattened convex; (b) lower part of fully opened flower, flattened convex.

(1) *Size.*—Average size when fully expanded — about 12 to 13 cm.

(2) *Borne.*—Singly, one to a stem.

(3) *Form.*—High centered, exhibition type, spiral imbricated, outer petals reflex and quill to points; mid petals reflex and roll under slightly.

(4) *Petalage.*—Many-petaled under normal conditions — fully double, about 25.

(5) *Color.*—When sepals part and petals begin to unfurl, color of petal top surface is near 57B to 57C, almost iridescent; at one-half to fully open stage petal top surface tends to near 51A to 51B and is more uniform in color than petal undersurface, which tends to be lighter-toned, near 51C to 51D and may show some veination and lightening toward base. Coloring at point of petal attachment is near 155A. Overall tonality from a distance is dark pink. Flowers are substantially nonfading upon aging.

(6) *Pedicel.*—Few to no hairs or prickles.
(7) *Fragrance.*—Slight to none.

C. Petals:
(1) *Texture.*—Medium.
(2) *Appearance.*—Inside velvety and outside satiny.
(3) *Form and size.*—Large, transverse elliptic.
(4) *Arrangement.*—Regularly arranged, imbricated.
(5) *Petaloids in center.*—Few to none.
(6) *Lasting quality.*—Long lasting quality on plant and after cutting.

REPRODUCTIVE ORGANS

A. Stamens, filaments and anthers:
*Arrangement and color.*—Regularly arranged around styles; color filaments yellow green.

B. Pollen:
*Color.*—Deep yellow.

C. Styles: Long, stigma above mouth of receptacle, red, only slightly hairy.

D. Stigmas: Positioned below anthers.

E. Hips: Funnel-shaped.

Plant

A. Form: Narrow upright, medium height.

B. Growth: Vigorous, about 1.8 meters in height.

C. Foliage: Compound 3, 5 and 7 leaflets.
(1) *Size.*—Medium to large.
(2) *Quantity.*—Abundant.
(3) *Color.*—Foliage at time of first flowering — medium to dark green, near 139A.

(4) *Shape.*—Oval, pointed.
(5) *Texture.*—Upper side is medium glossy; underside is matte.
(6) *Edge.*—Serrate.
(7) *Serration.*—Ordinary, acuminate apices.
(8) *Leaf stem.*—Color — medium green.
(9) *Stipules.*—Variable short to long, simple, medium to dark green, distinct auricle.
(10) *Leaflets.*—Cross section — slight convex; little to weak undulation at margin; terminal leaflet — medium length and width, rounded base; petiole — medium.
(11) *Stem length.*—About 80 cm.

D. Wood:
(1) *New wood.*—Color — young shoots have weak to medium anthocyanin. Coloration — bronze to reddish brown.
(2) *Old wood.*—Color — medium green.

E. Prickles (thorns):
(1) *Prickles.*—Present; quantity (main stalk) — ordinary; On laterals from stalk — ordinary; Shape of lower side — flat concave; Length — significant, about 7 mm; Color — tan to reddish tan; Position — irregular.

I claim:

1. A new and distinct variety of rose plant of the hybrid tea rose class, substantially as shown and described.

* * * * *

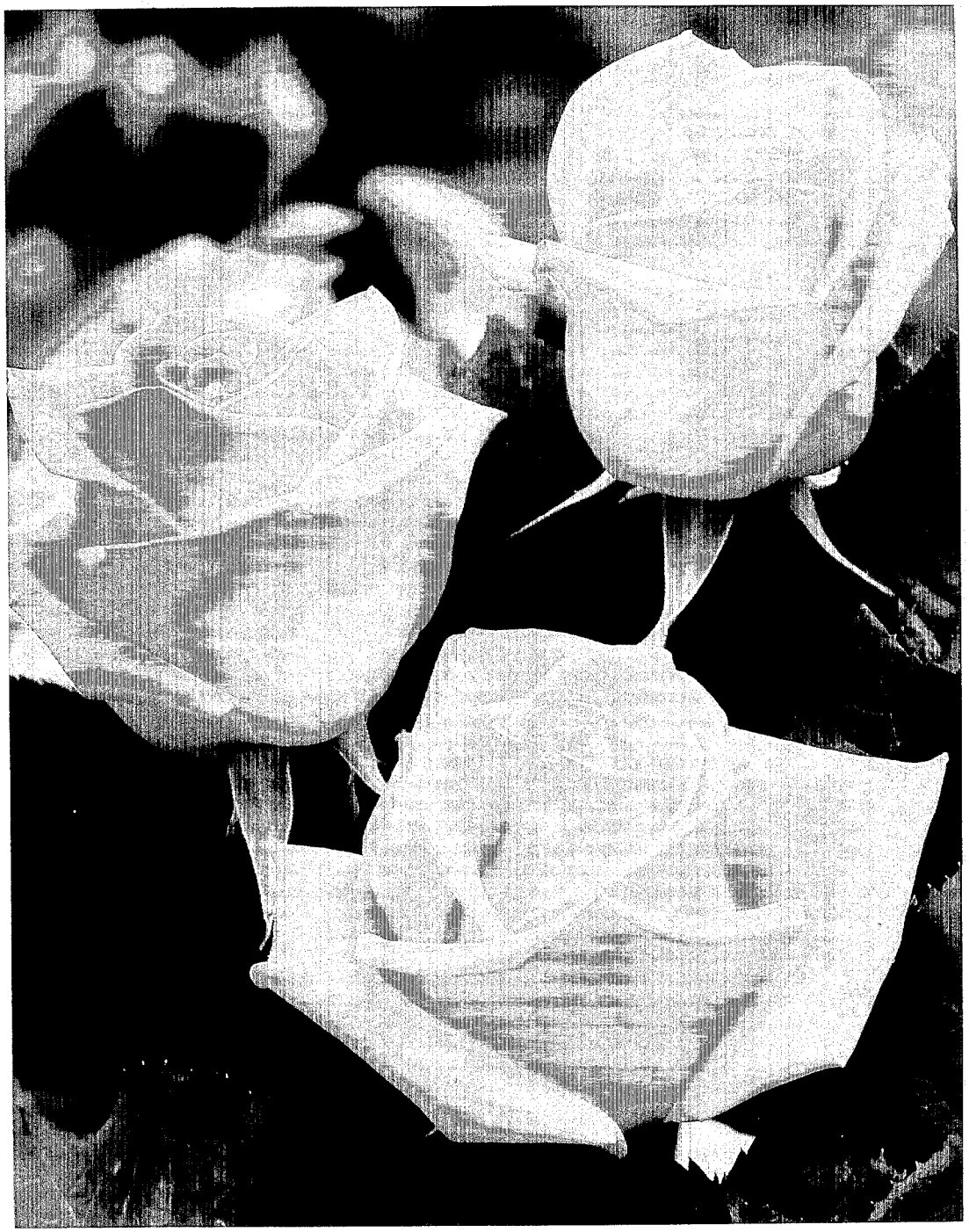

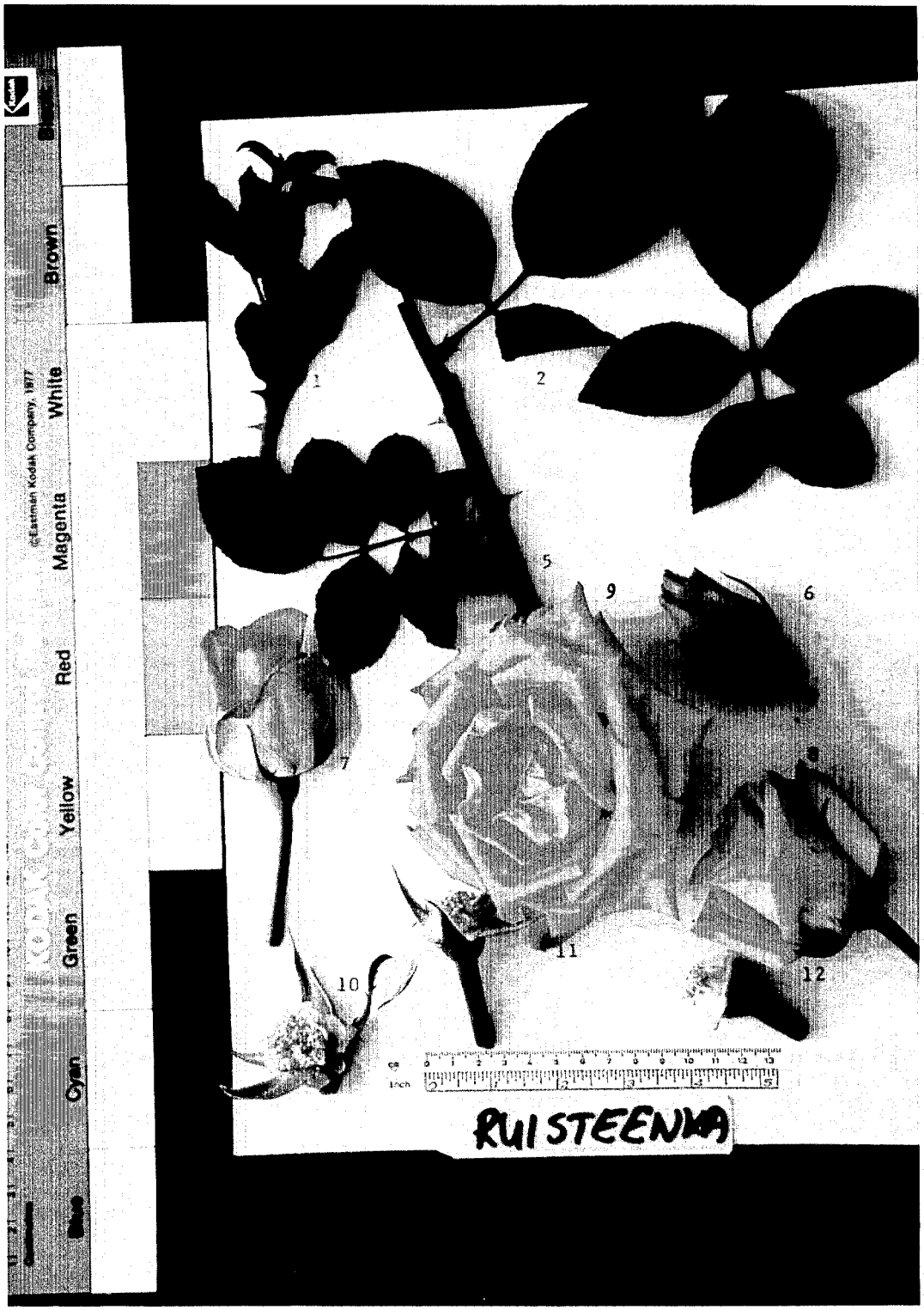
1
2
5
9
6
7
11
10
12
RUI STEENKA
Cyan
Green
Yellow
Red
Magenta
White
Brown
Blue
©Eastman Kodak Company, 1977

UNITED STATES PATENT AND TRADEMARK OFFICE

CERTIFICATE OF CORRECTION

PATENT NO. : Plant 8,632

DATED : March 8, 1994

INVENTOR(S) : J.E. Steenks

It is certified that error appears in the above-indentified patent and that said Letters Patent is hereby corrected as shown below:

On the Title Page:

[56] References Cited, U.S. PATENT DOCUMENTS, after "[58]" insert the following reference:
-- [56] Reference Cited
U.S. PATENT DOCUMENT
P.P. 7,362 10/1990 De Ruiter...Plt. 18 --.

Signed and Sealed this

Twenty-ninth Day of November, 1994

*Attest:*

Bruce Lehman

BRUCE LEHMAN

*Attesting Officer*

*Commissioner of Patents and Trademarks*